US007635375B2

(12) United States Patent
Borghi et al.

(10) Patent No.: US 7,635,375 B2
(45) Date of Patent: Dec. 22, 2009

(54) DEVICE FOR END-TO-SIDE ANASTOMOSIS

(75) Inventors: Enzo Borghi, Budrio (IT); Piergiorgio Tozzi, Lausanne (CH)

(73) Assignee: Newman Medical KFT, Budapest (HU)

( * ) Notice: Subject to any disclaimer, the term of this patent is extended or adjusted under 35 U.S.C. 154(b) by 191 days.

(21) Appl. No.: 11/020,903

(22) Filed: Dec. 22, 2004

(65) Prior Publication Data
US 2005/0149076 A1 Jul. 7, 2005

(30) Foreign Application Priority Data
Dec. 23, 2003 (IT) .......................... BO2003A0783

(51) Int. Cl.
*A61B 17/08* (2006.01)
(52) U.S. Cl. ..................................... 606/153
(58) Field of Classification Search ................ 606/151, 606/153–156; 623/1.35–1.36, 1.24–1.26
See application file for complete search history.

(56) References Cited

U.S. PATENT DOCUMENTS

| 6,254,618 | B1 * | 7/2001 | Dakov .......................... 606/153 |
| 6,451,034 | B1 * | 9/2002 | Gifford et al. ............... 606/153 |
| 6,652,540 | B1 | 11/2003 | Cole et al. |
| 7,182,771 | B1 * | 2/2007 | Houser et al. ............... 606/155 |
| 2004/0133221 | A1 * | 7/2004 | Sancoff et al. .............. 606/153 |
| 2005/0149075 | A1 * | 7/2005 | Borghi et al. ............... 606/153 |

FOREIGN PATENT DOCUMENTS

DE 102 05 997 A1 9/2003
FR 1 518 083 A 3/1968

OTHER PUBLICATIONS

International Search Report dated Apr. 11, 2005 corresponding to International Application No. PCT/IB2004/004259.

* cited by examiner

*Primary Examiner*—(Jackie) Tan-Uyen T Ho
*Assistant Examiner*—Melanie Tyson
(74) *Attorney, Agent, or Firm*—Fay Sharpe LLP

(57) ABSTRACT

A device for forming an end-to-side anastomosis of blood vessels includes a first body for engaging an end portion of a blood vessel, a second body having a saddle portion that may be placed partly over a wall of a side portion of a further blood vessel and having a central hole which communicates with the wall for stably engaging the side portion of the further blood vessel. The first and second body are engaged together and in the engaging portion there are provided piercing elements adapted to penetrate the external surface of the wall without penetrating the internal surface of the wall of the further blood vessel so as to avoid direct contact between the piercing elements and the blood inside the vessel.

20 Claims, 6 Drawing Sheets

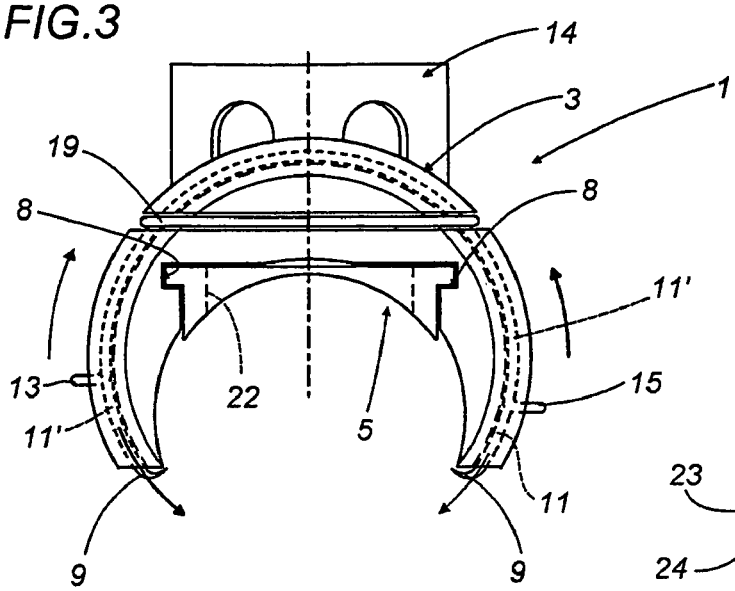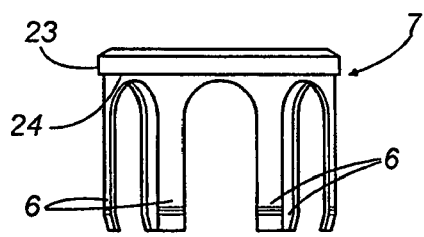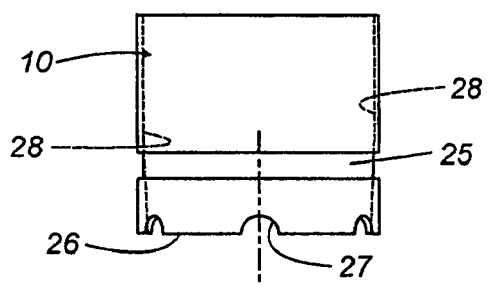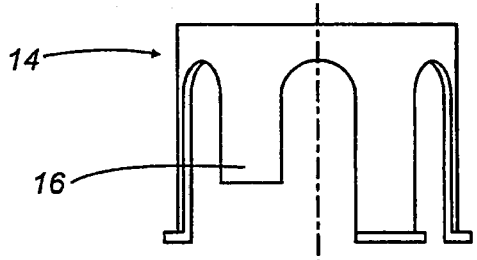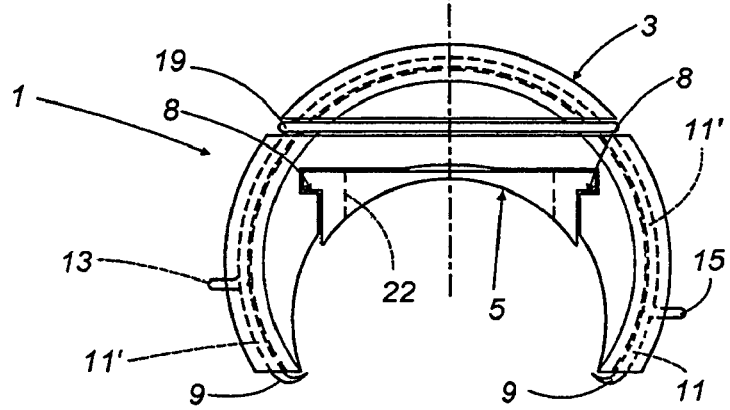

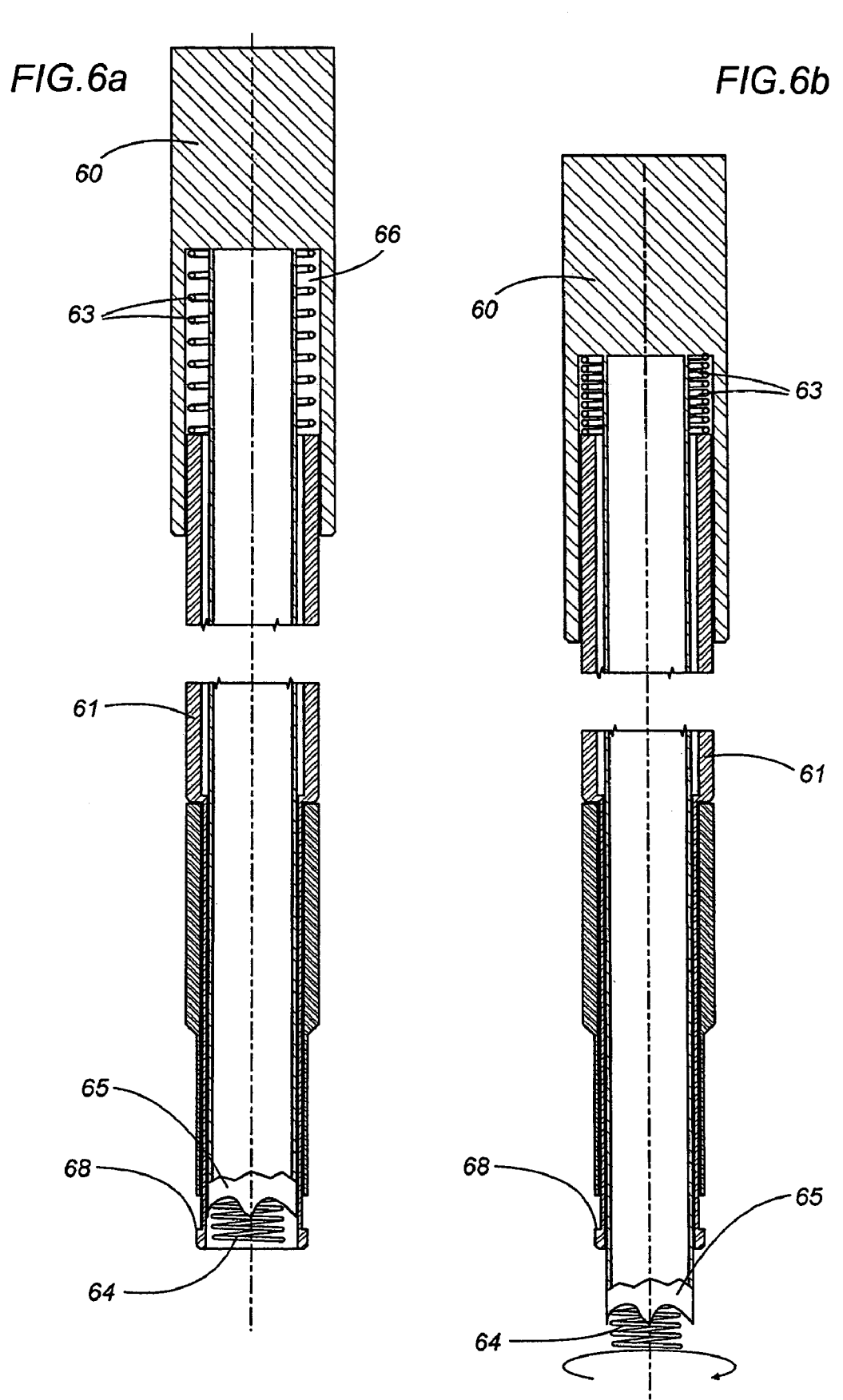

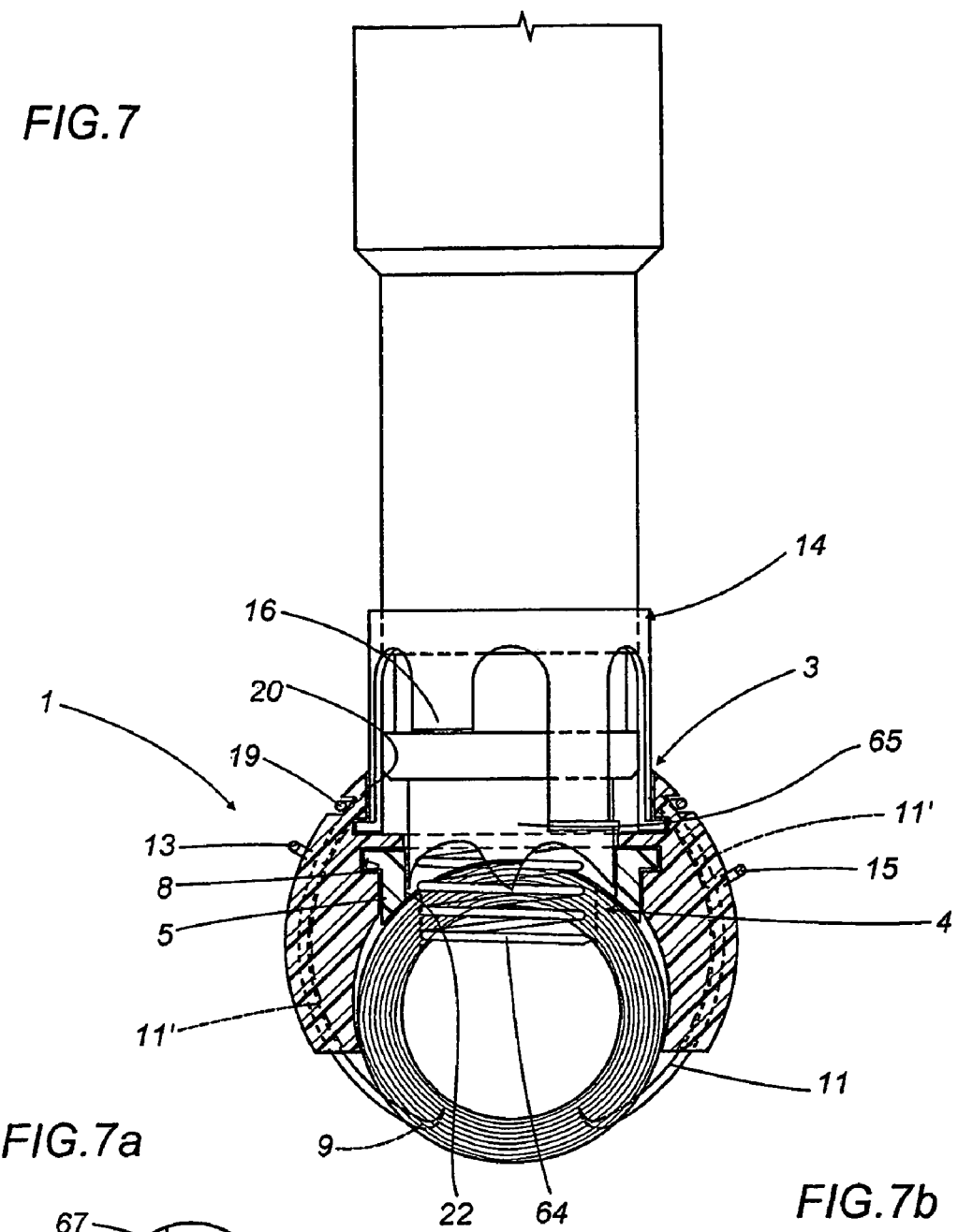
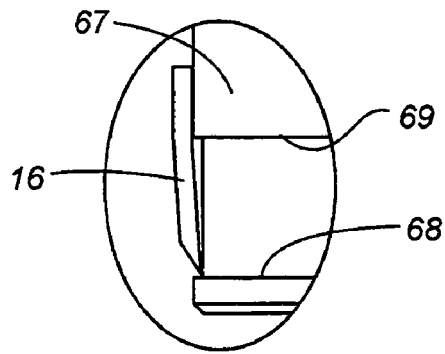
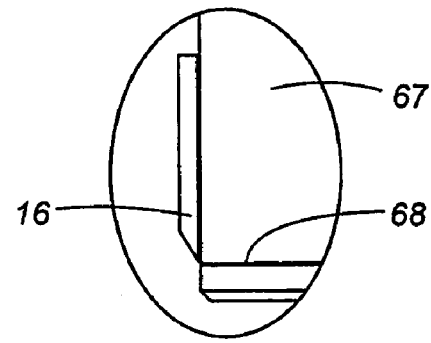
FIG.7
FIG.7a
FIG.7b

DEVICE FOR END-TO-SIDE ANASTOMOSIS

BACKGROUND OF THE INVENTION

The present invention relates to a device and method for anastomosis of blood vessels.

In surgery, the term "anastomosis" is used to mean a connection made surgically between two hollow structures.

This invention relates in particular to end-to-side anastomosis, where an end portion of a blood vessel is connected to a side portion of a vessel wall.

This specification expressly refers to vascular anastomosis applied to the human body, without thereby restricting the scope of the invention.

The earliest method of anastomosing two parts of a blood or lymphatic vessel consists in suturing the free ends of the vessel with thread.

This method, commonly known as suture anastomosis, has several disadvantages, the main one being that the suture produces a scar which, however small, prevents original flow from being perfectly restored to the vessel.

In this regard, it should be stressed that blood vessels are made up of several layers. The first, innermost layer, called endothelium, is covered by a second, middle layer called tunica media. The tunica media is in turn covered by a third layer, known as tunica adventitia.

It is therefore relatively easy for suturing to cause misalignment of some kind between the layers of one end of the vessel and the corresponding layers of the end of the other vessel. This is also a drawback in the case of lymphatic vessels which have a similar layered structure.

A second drawback is due to the fact that blood vessel suturing must be done by hand by a specialized surgeon because it is a complex operation that cannot be left to surgeons who are not highly skilled in this specific art.

Another known method of anastomosing two parts of a blood or lymphatic vessel is to use mechanical clamping devices designed to turn the ends to be connected inside out and to then join the inside walls of the vessel ends to each other.

This surgical technique (mechanical anastomosis by eversion), although simpler than suture anastomosis, is even less effective in re-establishing flow to the vessel.

For example, in the specific case of blood vessels, only the intimal layers are in contact with each other.

Besides this, mechanical anastomosis by eversion has other serious drawbacks which may be dangerous to a patient's health.

One drawback is due to the fact that everting the vessel ends may cause the ends to break, especially in the case of vessels larger than 3 mm in diameter whose walls are hardened by arteriosclerosis.

Another complication, specific to blood vessels, is caused by the fact that the inside layers of the vessel ends, after being turned inside out and placed side by side, are no longer exposed to the blood flow and therefore tend to atrophy, which in turn leads to narrowing of the blood vessel and reduction of the blood flow through it. The smaller the diameter of the vessel being operated on, the more serious this problem is.

In other mechanical anastomosis methods (such as the one described in U.S. Pat. No. 6,652,540) the two ends of the vessels to be joined are not placed in contact and, instead, metallic components are left in contact with the blood flowing through the vessel.

This produces an extremely dangerous condition which exposes the anastomosis to risk of immediate occlusion caused by the formation of a blood clot and narrowing of the anastomotic lumen.

Indeed, it has been found that contact between metal and blood tends to cause stenosis, that is to say, abnormal narrowing of the blood vessel, which may lead to total occlusion of the vessel in a period of 6 months to 1 year.

Those in the art have proposed to overcome this problem by chemically coating the metals with anti-stenosis substances, that is to say, substances that inhibit occlusions.

This solution has, however, produced serious problems because in many cases, the chemically coated metal parts in contact with the blood favor the formation of thrombi and the onset of acute thromboses that come sharply to a crisis, exposing patients to the risk of heart failure and, in some cases, leading to death.

Another drawback of prior art anastomosis devices is the complexity of applying them, especially to the side portions of the vessel. This means that the surgical operation involved tend to be very long, placing the patient at risk not only on account of the technical difficulty of the operation itself but also because of the likelihood of infection which increases with the increased length of time during which the body organs are exposed to the environment.

SUMMARY OF THE INVENTION

A first aim of the present invention is to provide a device and method for end-to-side anastomosis that overcomes the drawbacks and problems of prior art devices and method due to contact between the metal or artificial parts and the blood.

Another aim of the invention is to propose an anastomosis apparatus that permits flow in the blood vessel to be re-established more effectively than prior art devices.

A further aim of the invention is to provide a device that is simple to use and minimizes blood loss during the operation without interrupting blood flow in the vessel whose side is anastomosed.

These aims are achieved by an apparatus and method according to the main claims.

A first advantage of the invention is that contact between the connecting parts and the blood vessel is limited to the vessel wall, leaving the inside surface free, and there is therefore no contact with the blood inside the vessel.

Another advantage is that there is no contact between the device and the cut edge of the wall of the anastomosed vessel, which permits the intima of the two vessel parts to be joined in optimum manner.

A yet further aim of the invention is to propose a simplified anastomosis apparatus whose use can be learned in a very short time and which permits the formation of anastomoses of constant quality.

A still further aim of the invention is to propose an anastomosis apparatus that reduces the time required for the anastomosis operation.

BRIEF DESCRIPTION OF THE DRAWINGS

The invention will now be described with reference to the accompanying drawings which illustrate a preferred embodiment of it and in which:

FIG. 3 is a front view of the device of FIG. 1;

FIG. 4 is an exploded view of the device of FIG. 3 in combination with a device for end-to-end anastomosis;

FIGS. 6a and 6b show a circular scalpel for end-to-side anastomosis applications in a retracted configuration and in an extracted, cutting configuration, respectively;

FIG. 7 shows the scalpel of FIGS. 6a, 6b applied to a device according to FIGS. 1 to 3;

FIGS. 7a, 7b show a detail of the elements for clamping the device of FIGS. 1 to 3 to the scalpel of FIG. 7, in a clamped and unclamped configuration, respectively;

DESCRIPTION OF THE PREFERRED EMBODIMENTS

Figure 1:
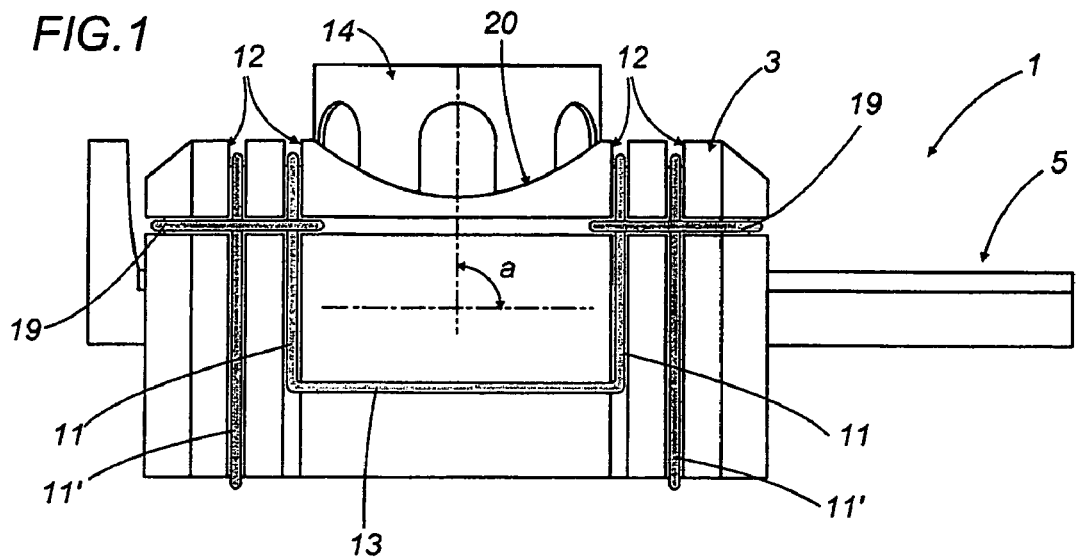
FIG. 1 is a side view of a device according to the present invention.
Figure 2:
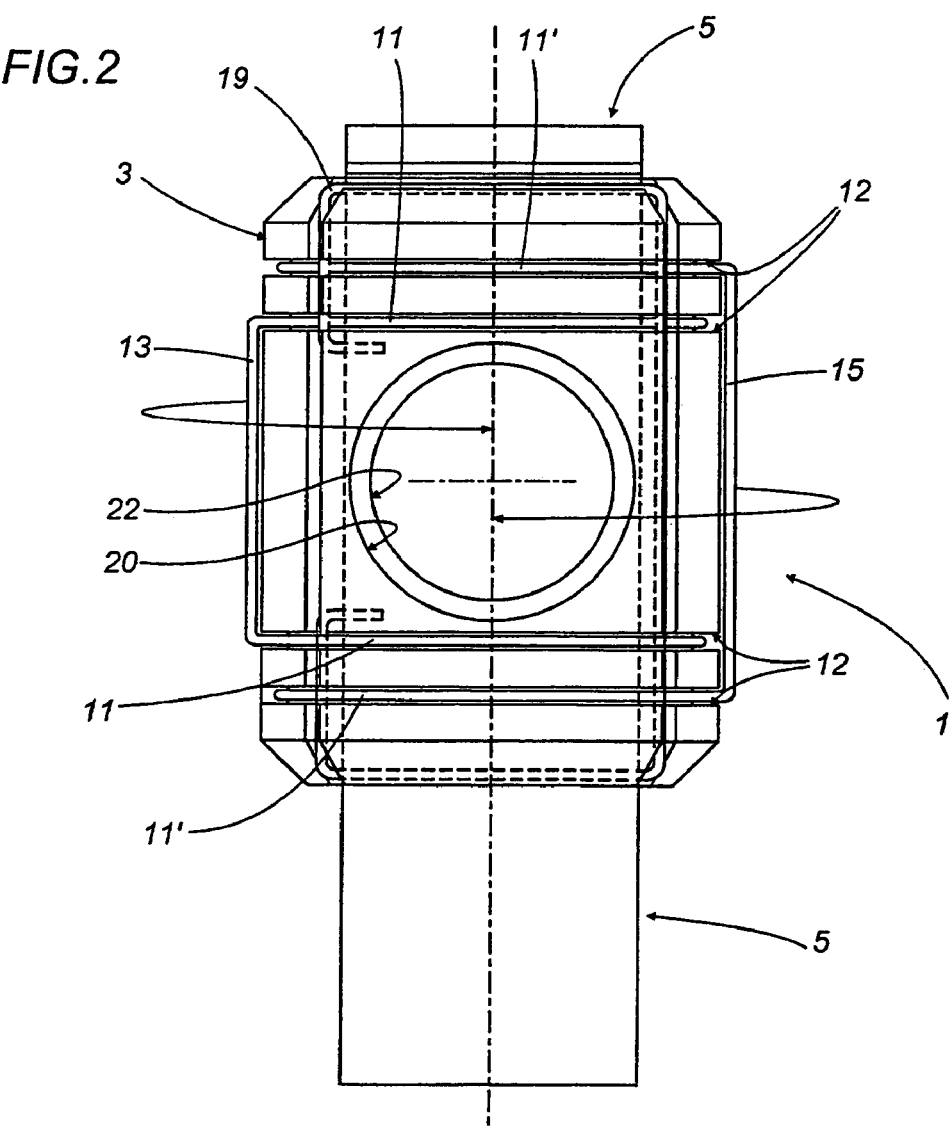
FIG. 2 is a top view of the device of FIG. 1.

With reference the accompanying drawings, a device according to the invention comprises a body 1, clearly shown in FIGS. 1 to 3, for connecting a side wall portion 4 of an anastomosed vessel.

In the preferred embodiment described here, the body 1 comprises an approximately semicylindrical or "saddle-shaped" element 3 designed to be placed at least partly over the portion 4 and having a central hole 20 in which there is positioned and fixed a cylindrical element 14 whose axis "a" makes an angle, preferably, of 90°, 60°, 45° or 30° with the longitudinal axis of the saddle-shaped portion 3 or of the portion 4 of the anastomosed vessel.

The body 1 also comprises a gate valve 5 slidable lengthwise along internal grooves 8 made in the saddle 3 and having a hole 22 in it, this hole 22 being such that, during use, it is alternately aligned with and offset from the hole 20 in the saddle 3, in such a manner as to open and close the hole 20, respectively.

The inside of the valve 5 preferably has a curved, circular profile which facilitates its sliding into contact with the blood vessel wall and which can be taken right out of the grooves 8.

For attaching the blood vessel, the saddle 3 comprises fixing means consisting of claws 9 designed to clutch the outside wall of the portion 4.

In this embodiment, the claws 9 are made by bending the free pointed ends of two essentially U-shaped lengths 11, 11' of wire.

The side arms of the "U" can slide along respective grooves 12 made in the outside surface of the saddle 3, while the central sections 13, 15 joining the side arms of the "U" protrude from the outside surface of the saddle and can be accessed by the surgeon.

Preferably, the wires 11, 11' are held in place by another wire 16 positioned in collar-like fashion around the saddle 3 to prevent the wires 11 and 11' coming out of the grooves 12.

During application to a side portion 4 of an anastomosed vessel, the saddle-shaped element 3 of the body 1 is first placed over the wall of the vessel 1 with the hole 22 of the gate valve 5 preferably in the open position, that is to say, aligned with the hole 20 in the saddle-shaped element 3.

Next, the surgeon, by acting on the sections 13, 15 of the wires 11, 11' extends the claws 9 as far as possible (in the direction indicated by the arrows in FIG. 3) and then retracts them again in such a way that the claws 9 penetrate the wall of the vessel 1 (FIGS. 5a and 5b) and securely connect the body 1 to the vessel wall 4.

At this point, the body 3 is securely attached to the vessel portion 4 and the vessel itself can be incised using a suitable scalpel with a circular head capable of cutting and removing the vessel tissue at the hole 20.

Preferably, the hole can be made using the scalpel illustrated in FIGS. 6a, 6b and 7, 7a, 7b.

The scalpel consist of a control rod 60 having at a first end of it a helical element 64 and a cup-shaped blade 65 positioned coaxially on the outside of the helical element 64.

The rod 60 can both turn freely and slide lengthwise in a coaxial cylindrical sleeve 61 against the force of an opposing spring 63 housed in a crown-shaped cylindrical chamber 66 made in the second end of the rod 60.

The front end of the sleeve 61 has a protrusion 68 whose diameter is substantially the same as the inside diameter of the element 14 and with which it may be aligned precisely, since it has the same outside diameter, with the head 69 of an outside cylindrical slider 67 that is slidable along the sleeve 61.

During use, the scalpel rod 60 is initially in the retracted position (FIG. 6a) since the spring 63 keeps it all the way inside the sleeve 61.

In this configuration, the front end of the sleeve 61 is inserted into the cylindrical element 14 until it engages the protrusion 68 with tabs 16 extending from the cylinder 14 (FIG. 7a) in such a way as to hold the scalpel in place.

The rod 60 is now advanced, against the force of the spring 63, and at the same time turned in such a way as to impart a twisting movement on the helix 64 causing the helix to pierce the vessel wall 1 of the portion 4 and enabling the cup-shaped blade 65 to make an incision at the hole 22 in the saddle 3 and at the hole 20 in the valve 5.

At this point, by releasing and retracting the rod 60 without twisting it, the helix is made to take the cut portion of the wall 1 out with it and the gate valve 5 can be closed to restore the geometrical continuity of the vessel wall with the minimum of blood loss.

Once the cut at the hole 22 has been made, the scalpel can be removed by advancing the head 69 of the slider 67 until it is against the protrusion 68, thus disengaging the tabs 16 (FIG. 7b) and allowing the scalpel to be taken out of the element 14.

Figure 5A:
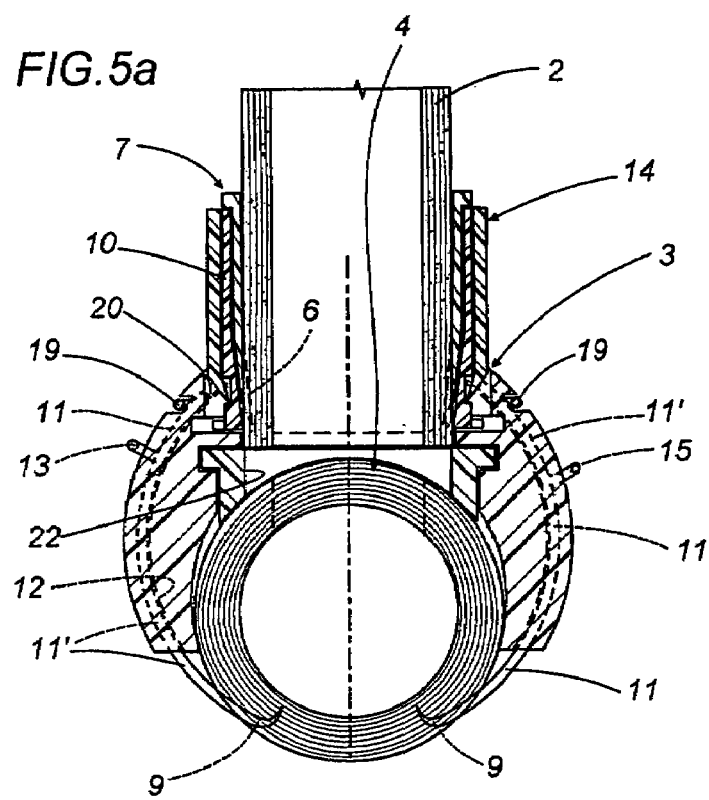
FIGS. 5a and 5b are, respectively, a partial section and a full side view of the device of FIG. 4.
Figure 5B:
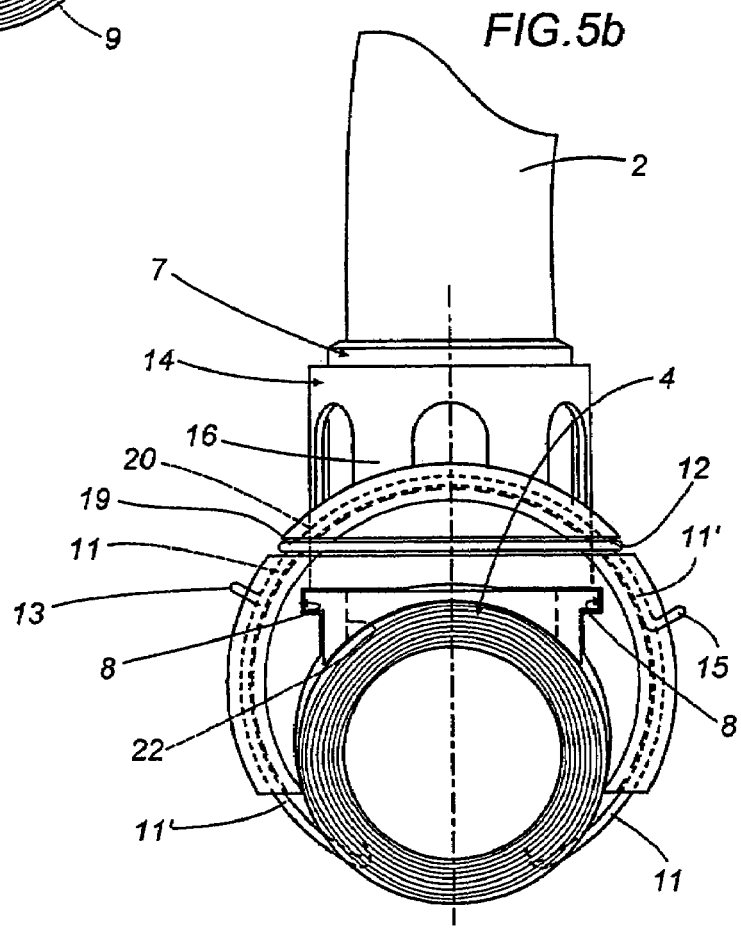

FIGS. 4 and 5a, 5b illustrate a preferred form of connection between the body 1 and an end portion 2 of the anastomosed vessel with a respective end connection device.

It will be understood that the side connection device according to the invention may also be used in combination with other types of end connection devices.

In the embodiment described here, the apparatus according to the invention comprises a first internal cylindrical element, or "circular staple", 7 for grasping the an end portion 2 of the blood vessel to be anastomosed, and a second cylindrical element 10 designed to securely engage the internal element 7.

Looking in more detail, the internal cylindrical element 7 consists of an uninterrupted ring-shaped part 23 which has a plurality of longitudinal legs 6 extending from the front of it and whose outside surface has an annular protrusion or stop lip 24.

The middle cylindrical element 10 has an outside diameter equal to the outside diameter of the ring 23 and, on its outside surface, has an annular recess 25 designed to engage the tabs 16 of the cylinder 14.

Further, the inside diameter of the middle cylinder 10 is that the latter can slide over the inner cylinder 7, with slight mechanical interference, until it comes to a stop against the protrusion 24.

Inside, the cylinder 10 has a tapered profile 28 that converges towards its front portion 26, so that the inside diameter at the free edge of the front portion 26 substantially coincides with the inside diameter of the first cylinder 7.

Preferably, the front portion 26 of the cylinder 10 also has a set of semicircular indentations 27.

Below is a description, with reference to FIG. 2, of how the device is applied to the end portion 2 to be joined.

In the working configuration of the device, illustrated in FIGS. 5a and 5b, a cylinder 7 with the legs 6 facing the free edge 25 of the wall 1 is connected to the end portion 2, and a middle cylinder 10 is then made to slide over the cylinder 7 until stopping against the protrusion 24.

To enable the inner cylinder 7 to grasp the wall 2, the cylinder 7 is made to slide lengthwise in the middle cylinders 10 in such a way that the legs 6, initially coaxial or slightly divergent, are made to bend inwards by contact with the tapered profile 28 so that they converge towards the inside of the cylinder 7, pressing against the surface of the wall 2 and penetrating the latter close to the free edge 25.

Advantageously, the depth to which the legs 6 penetrate the vessel wall is determined by the special shape of the legs 6 and cylinder 10, which is such that the legs do not go right through the vessel wall, thus avoiding contact with the blood inside the vessel.

As illustrated in FIGS. 5a, 5b, once the part of the device consisting of the cylinders 7 and 10 has been connected to the vessel end portion 2, application of the device can be completed by connecting that part to the body 1 by simply inserting the cylinder 10 into the connecting element 14 until the tabs 16 snap into the recess 25 and the gate valve 5 can be opened again and, if necessary, removed.

Figure 8A:
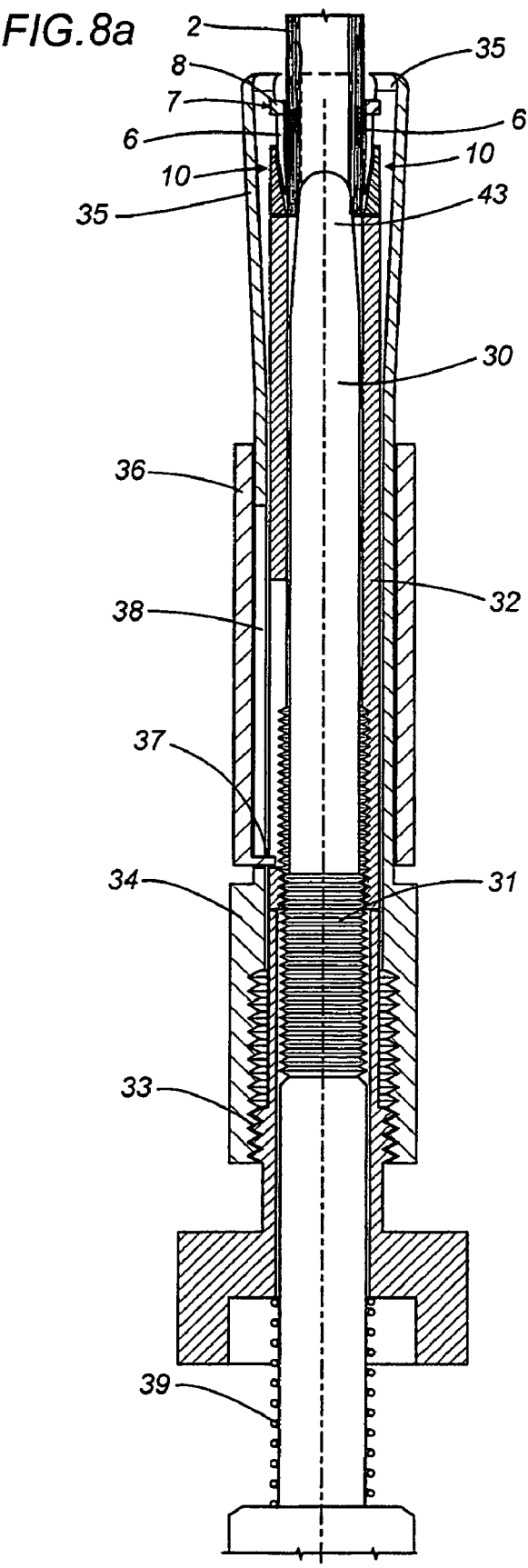
FIGS. 8a and 8b show a possible applicator for implanting an anastomosis device to an end portion of a blood vessel.
Figure 8B:
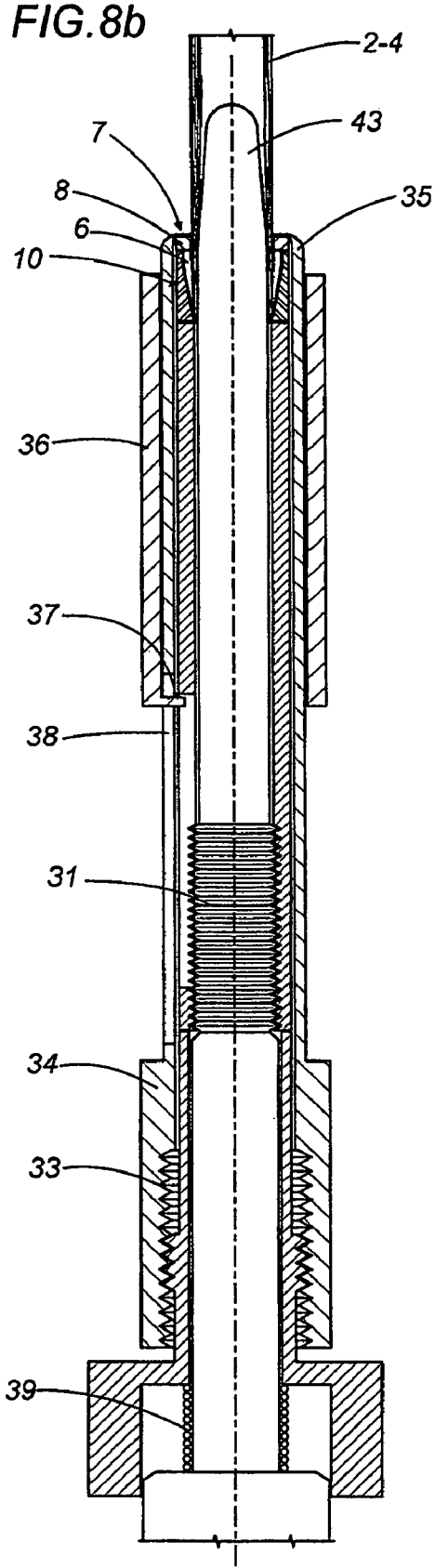

Described below with reference to FIGS. 8a, 8b is an applicator apparatus for implanting a device according to the invention to the end portion 2 of a blood vessel.

Although the applicator described below is the tool to be used preferably for this purpose, it will be understood that other types of applicators may be used without departing from the scope of the invention.

The applicator comprises a rod 30 which is equipped at one end with a nosepiece 43 of measured diameter and which, by means of a threaded coupling 31, can be screwed into a hollow piston 32 against the action of a spring 39.

The piston 32 is in turn slidable, by means of a second screw coupling 33, inside a hollow body 34, whose top end has a number of flexible tabs 35 normally spread outwards and extending frontally past the nosepiece 43.

A slider 36 can also move on the outside of the hollow body 34, constrained by a tooth 37 that slides in a longitudinal groove 38 made in the body 34.

The slider 36 can adopt a first position in which the tabs are spread apart (FIG. 8a) and a second end position (FIG. 8b) in which the slider has moved towards the end of the body 34 and forced the tabs 35 to converge and close.

To use the applicator, a cylinder 10 is inserted into it through the opening defined by the tabs 35 until the front portion 26 stops against the head 41 of the piston 32.

Next, a circular staple 7 is partially inserted into the cylinder 10 without forcing and the tabs 35 are closed and positioned at the back in such a way as to hold the ring portion 8 of the circular staple 7.

By operating the applicator, the surgeon inserts an end portion of a vessel 2 through the circular staple 7 and the cylinder 10 until the edge 25 of the vessel 2 is made to touch on the head 42 of the piston 32.

Preferably, the front portion 26 of the cylinder 10 also has a set of semicircular indentations 27 which, during use, ensure that the vessel end portion 2, 4 to which the device is applied is correctly positioned.

Advantageously, the indentations 27 of the cylinder 10 ensure that the vessel wall has stopped against the piston 32.

By operating on the grip 40 of the rod 30, it is now possible to advance the nosepiece 43 into the vessel 2 in such a way that the vessel remains precisely clamped between the nosepiece 43 itself and the inside surface at the front of the cylinder 10.

The nosepiece is preferably variable in diameter and consists, for example, of a helical wire winding extending in the direction of the rod 30, where the two ends of the helix can turn relative to each other in such a way so as to move closer together/apart and thus vary the radial dimension of the winding.

By twisting the grip 41 of the piston 32, the surgeon can now advance the piston relative to the tab body so that the tabs and the piston come into contact and clamp the circular staple 7 within the cylinder 10.

As described above, when the legs 6 come into contact with the tapered inside surface 28 of the cylinder 10, they are forced to converge and partially penetrate the vessel wall 2.

Once clamped by the piston 32, the staple 7 is held by interference in the cylinder 10, whilst the vessel wall 2 is retained frontally and radially by the legs 6, with the edge 25 flush with or just protruding from the front 26 of the cylinder 10 and with an internal diameter or lumen defined by the size of the nosepiece 43 used.

At this point, it is sufficient to twist the piston 32 in the opposite direction to retract the slider 36 to open the tabs 35 and release the applicator from the vessel wall while leaving the device in place.

From the above description, experts in the trade will no doubt appreciate the advantages of joining both the end portion and the side portion of the anastomosed parts in such a way that the free edges are held in close contact with each other without extraneous elements preventing proper healing of the tissue or inducing the formation of stenosis or thrombi in the blood vessel.

It is therefore evident that, under these conditions, optimum flow is re-established naturally in the blood vessel without external elements or interruptions leading to the above mentioned vessel healing difficulties and to the possible formation of stenosis due to the contact of extraneous elements with the blood.

Further, the anastomosed blood vessel has no foreign objects protruding on the inside of it to interrupt the continuity of its lumen, with the advantage of not contaminating the blood or reducing normal blood flow.

Moreover, in the embodiment described with reference in particular to FIG. 5a, the legs 6 keep the vessel wall at a precisely measured diameter, which is preferably the same as that of the hole 22 made in it, so that the size and position of the free edges of both the side and end portions are aligned exactly, thus favoring proper healing of the vessel tissue.

In particular, the invention may also be generally applied to different ducts of the human body other than blood vessels.

In addition it has to be understood that the invention also involves advantages in the surgery tecnique for anastomosis and it makes possible to intervene for example by laparoscopic method in a low-invasive way.

This invention has been described with reference to preferred embodiments of it but it will be understood that it may be modified and adapted in several ways without thereby departing from the scope of the inventive concept.

What is claimed is:

1. A device for forming an end-to-side anastomosis, said device comprising first means for engaging an end portion of a blood vessel or of a prosthesis, second means for stably engaging a side portion of a further blood vessel or of a further prosthesis, and means for reciprocally connecting the first and second means for engaging, the second means for engaging comprising two claws for grasping said side portion and adapted to only partially penetrate the side portion of said further blood vessel or said further prosthesis so as to avoid direct contact between the claws and the blood inside the vessel or prosthesis, wherein said claws include bent free pointed ends of two essentially U-shaped lengths of wire, wherein side arms of each U-shaped length of wire are slidable along respective grooves in an outside surface of the second means for engaging, while the central section of each U-shaped length of wire is adapted to be accessed by a surgeon.

2. A device for forming an end-to-side anastomosis, said device comprising first means for engaging an end portion of a blood vessel or of a prosthesis, second means for stably engaging a side portion of a further blood vessel or of a further prosthesis, and means for reciprocally connecting the first and second engagement means, the second engagement means comprising two piercing elements adapted to only partially penetrate a side wall of said further blood vessel or said further prosthesis so as to avoid direct contact between the piercing elements and the blood inside the vessel or prosthesis, wherein the device further comprises a valve that can be actuated in such a way as to shut off a hole of the second engagement means communicating with the side wall, the valve being a gate valve with a valve hole in it and being mobile lengthwise along internal grooves in the second engaging means so that, during use, the valve hole is alternately aligned with the hole in the second engaging means or offset from the hole in the second engaging means in such a way as to close it.

3. A device for forming an end-to-side anastomosis, said device comprising first engagement means for engaging an end portion of a blood vessel or of a prosthesis, second engagement means comprising a saddle portion to be placed at least partly over a wall of a side portion of a further blood vessel or of a further prosthesis and having a central hole which communicates with the wall for stably engaging said side portion of said further blood vessel or said further prosthesis, and means for reciprocally connecting the first and second engagement means, wherein the second engagement means comprises two piercing elements adapted to penetrate an external surface of said wall without penetrating an internal surface of said wall of said further blood vessel or said further prosthesis so as to avoid direct contact between the piercing elements and blood inside the further blood vessel or the further prosthesis, wherein said piercing elements comprise claws that move relative to the saddle and that can be actuated in such a way as to grasp the wall, wherein the claws include bent free pointed ends of two essentially U-shaped lengths of wire, and wherein side arms of each U-shaped length of wire are slidable along respective grooves in an outside surface of the saddle, while a central section of each U-shaped length of wire is adapted to be accessed by a surgeon.

4. The device according to claim 3, comprising a valve that can be actuated in such a way as to shut off the hole.

5. The device according to claim 4, wherein the valve is a gate valve with a valve hole in it and is mobile lengthwise along internal grooves in the saddle so that, during use, the valve hole is alternately aligned with the hole in the saddle or offset from the hole in the saddle in such a way as to close it.

6. The device according to claim 4, wherein the valve is removable.

7. The device according to claim 3, wherein the first engagement means comprises a first cylindrical element including a ring and a plurality of longitudinal legs extending from the front of the ring and designed to partially pierce the vessel wall or prosthesis at a front edge of its end portion.

8. The device according to claim 7, wherein the first engagement means comprises a second cylindrical element whose inside surface has a tapered profile that converges towards its front portion so as to bend the legs inwards towards each other when the first cylindrical element is inserted into the second cylindrical element.

9. The device according to claim 8, wherein the front portion has a set of semicircular indentations.

10. The device according to claim 8, wherein the first cylindrical element can be inserted into the second cylindrical element until the second cylindrical element comes into contact with an outer stop lip on the ring designed to prevent the first cylindrical element from sliding lengthwise further into the second cylindrical element.

11. The device according to claim 7, wherein the first cylindrical element can be inserted into the second cylindrical element stably by mechanical interference.

12. The device according to claim 3, wherein the means for reciprocally connecting the first and second engagement means comprises a cylindrical element that is attached to the saddle and communicates with the hole and whose axis makes an angle of 90°, 60°, 45° or 30° with the longitudinal axis of the saddle.

13. The device according to claim 12, wherein the means for reciprocally connecting comprises snap fixing means between the first and second engagement means.

14. The device according to claim 13, wherein the snap fixing means comprises at least one deformable tab on the cylindrical element, protruding slightly into the cylindrical element in such a way as to snap into an external annular recess made in an outside surface of the cylindrical element.

15. A device for forming an end-to-side anastomosis, said device comprising first engagement means for engaging an end portion of a blood vessel or of a prosthesis, second engagement means comprising a saddle portion to be placed at least partly over a side wall of a side portion of a further blood vessel or of a further prosthesis and having a central hole which communicates with the side wall for stably engaging said side portion of said further blood vessel or said further prosthesis, and means for reciprocally connecting the first and second engagement means, wherein the second engagement means comprises two piercing elements adapted to penetrate an external surface of said side wall without penetrating an internal surface of said side wall of said further blood vessel or said further prosthesis so as to avoid direct contact between the piercing elements and blood inside the further blood vessel or the further prosthesis, the device further comprising a valve that can be actuated in such a way as to shut off the hole, wherein the valve is a gate valve with a valve hole in it and is mobile lengthwise along internal grooves in the saddle so that, during use, the valve hole is alternately aligned with the hole in the saddle or offset from the hole in the saddle in such a way as to close it.

16. The device according to claim 15, wherein said piercing elements comprise claws that move relative to the saddle and that can be actuated in such a way as to grasp the side wall.

17. The device according to claim 16, wherein the claws include bent free pointed ends of two essentially U-shaped lengths of wire, wherein side arms of each U-shaped length of wire are slidable along respective grooves in an outside surface of the saddle, while a central section of each U-shaped length of wire is adapted to be accessed by a surgeon.

18. The device according to claim 15, wherein the first engagement means comprises a first cylindrical element including a ring and a plurality of longitudinal legs extending from a front of the ring and designed to partially pierce a wall of the end portion of the vessel or prosthesis at a front edge of the end portion.

19. The device according to claim 15, wherein the means for reciprocally connecting the first and second engagement means comprises a cylindrical element that is attached to the saddle and communicates with the hole and whose axis makes an angle of 90°, 60°, 45° or 30° with the longitudinal axis of the saddle.

20. The device according to claim 15, wherein the valve is removable.

* * * * *